US006214363B1

(12) United States Patent
Beerse et al.

(10) Patent No.: US 6,214,363 B1
(45) Date of Patent: *Apr. 10, 2001

(54) LIQUID ANTIMICROBIAL CLEANSING COMPOSITIONS WHICH PROVIDE RESIDUAL BENEFIT VERSUS GRAM NEGATIVE BACTERIA

(75) Inventors: Peter William Beerse, Maineville; Jeffrey Michael Morgan, Springboro; Kathleen Grieshop Baier, Cincinnati; Robert Gregory Bartolo, Montgomery; Theresa Anne Bakken, Cincinnati; Mary Elizabeth Carethers, West Chester; Mark Richard Sine, Morrow; Mannie Lee Clapp, Mason; Raphael Warren, Amberly Village, all of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/969,077

(22) Filed: Nov. 12, 1997

(51) Int. Cl.[7] ............................. A01N 25/34; A61K 6/00; A61K 7/50; A61K 7/40
(52) U.S. Cl. ......................... 424/404; 424/401; 510/130; 510/131; 510/138; 510/155
(58) Field of Search ................................ 424/404, 401; 510/130, 131, 138, 155; 514/162, 859

(56) References Cited

U.S. PATENT DOCUMENTS

| | | | |
|---|---|---|---|
| 2,999,265 | 9/1961 | Duane et al. | 424/16 |
| 3,057,467 | 10/1962 | Williams | 206/46 |
| 3,141,821 | 7/1964 | Compeau | 167/58 |
| 3,256,200 | 6/1966 | Reller et al. | 252/106 |
| 3,326,808 | 6/1967 | Noseworthy | 252/106 |
| 3,398,826 | 8/1968 | Clancy | 206/46 |
| 3,563,371 | 2/1971 | Heinz | 206/46 |
| 3,650,964 | 3/1972 | Sedliar et al. | 252/106 |
| 3,835,057 | 9/1974 | Cheng et al. | 252/107 |
| 3,867,300 | 2/1975 | Karabinos et al. | 252/106 |
| 3,881,210 | 5/1975 | Drach et al. | 15/104.93 |
| 3,969,258 | 7/1976 | Carandang et al. | 252/106 |
| 4,045,364 | 8/1977 | Richter | 252/106 |
| 4,062,976 | 12/1977 | Michaels | 424/319 |
| 4,067,997 | 1/1978 | Kabara | 424/312 |
| 4,075,350 | 2/1978 | Michaels | 424/316 |
| 4,105,783 | 8/1978 | Yu et al. | 424/283 |
| 4,107,328 | 8/1978 | Michaels | 424/316 |

(List continued on next page.)

FOREIGN PATENT DOCUMENTS

| | | | |
|---|---|---|---|
| 0037224 A1 | 10/1981 | (EP) | C11D/3/48 |
| 0368146 | 5/1990 | (EP) | C11D/3/50 |
| 0403304 | 12/1990 | (EP) | A61K/7/06 |
| 0 613 675 | 9/1994 | (EP) | A61K/7/00 |
| 0619074 A1 | 10/1994 | (EP) . | |
| 0670158 A2 | 9/1995 | (EP) | A61K/7/50 |
| 2288811 | 11/1995 | (GB) | C11D/1/831 |
| 2530661 | 6/1996 | (JP) | A61K/7/50 |
| WO 92/18100 | 4/1992 | (WO) | A61K/7/50 |
| WO 93/17558 | 9/1993 | (WO) | A23L/2/38 |
| WO94/06440 | 9/1993 | (WO) | A61K/31/74 |
| WO94/18292 | 8/1994 | (WO) | C11D/1/66 |
| WO 95/03028 | 2/1995 | (WO) | A61K/7/00 |
| WO 95/03781 | 2/1995 | (WO) | A61K/7/48 |
| WO 95/32705 | 5/1995 | (WO) | A61K/7/50 |
| WO 95/24179 | 9/1995 | (WO) | A61K/7/00 |
| WO 96/06152 | 2/1996 | (WO) | C11D/3/00 |
| WO 96/06153 | 2/1996 | (WO) | C11D/3/00 |
| WO 96/29049 | 2/1996 | (WO) | A61K/7/48 |
| WO 96/17918 | 6/1996 | (WO) | C11D/1/83 |
| WO 96/21426 | 7/1996 | (WO) | A61K/7/50 |
| WO 96/25913 | 8/1996 | (WO) | A61K/7/16 |
| WO 96/29983 | 10/1996 | (WO) | A61K/7/50 |
| WO97/00676 | 1/1997 | (WO) | A61K/31/19 |
| WO 97/03647 | 2/1997 | (WO) | A61K/7/50 |
| WO 97/07781 | 3/1997 | (WO) | A61K/7/50 |
| WO 97/09957 | 3/1997 | (WO) | A61K/7/00 |
| WO 97/14406 | 4/1997 | (WO) | A61K/7/50 |
| WO 97/16066 | 5/1997 | (WO) | A01N/25/04 |
| WO 97/16168 | 5/1997 | (WO) | A61K/7/50 |
| WO 98/18445 | 5/1998 | (WO) | A61K/7/50 |

OTHER PUBLICATIONS

U.S application No. 08/738,194, Fowler et al., filed Oct. 25, 1996.
U.S. application No. 08/738,669, Fowler et al., filed Oct. 25, 1996.
U.S. application No. 08/738,668, Fowler, filed Oct. 25, 1996.

(List continued on next page.)

Primary Examiner—Frederick Krass
Assistant Examiner—Donna Jagoe
(74) Attorney, Agent, or Firm—Tara M. Rosnell; Stephen T. Murphy

(57) ABSTRACT

The present invention relates to a rinse-off antimicrobial cleansing composition comprising from about 0.001% to about 5% of an antimicrobial active, from about 1% to about 80% of an anionic surfactant, from about 0.1% to about 12% of a proton donating agent; from about 0.1% to about 30% of a deposition aid; and from about 3% to about 98.8% of water, wherein the composition is adjusted to a pH of from about 3.0 to about 6.0, wherein the rinse-off antimicrobial cleansing composition has a Gram Negative Residual Effectiveness Index of greater than about 0.3, and wherein the rinse-off antimicrobial cleansing composition has a Mildness Index of greater than 0.3. The invention also encompasses methods for cleansing skin and providing residual effectiveness versus Gram negative bacteria using these products.

29 Claims, No Drawings

U.S. PATENT DOCUMENTS

| | | | |
|---|---|---|---|
| 4,118,332 | 10/1978 | Apostolatos et al. | 252/107 |
| 4,183,952 | 1/1980 | Michaels | 424/320 |
| 4,404,040 | 9/1983 | Wang | 134/22.14 |
| 4,406,884 | 9/1983 | Fawzi et al. | 424/81 |
| 4,512,987 | 4/1985 | Schindlery | 514/171 |
| 4,514,385 | 4/1985 | Damani et al. | 424/81 |
| 4,518,593 | 5/1985 | Juvin et al. | 424/195 |
| 4,715,980 | 12/1987 | Lopes et al. | 252/106 |
| 4,732,756 | 3/1988 | Johnson et al. | 428/74 |
| 4,732,797 | 3/1988 | Johnson et al. | 428/74 |
| 4,781,974 | 11/1988 | Bouchette et al. | 428/288 |
| 4,820,698 | 4/1989 | Degenhardt et al. | 514/102 |
| 4,822,604 | 4/1989 | Knoll et al. | 424/70 |
| 4,847,072 | 7/1989 | Bissett et al. | 424/59 |
| 4,891,227 | 1/1990 | Thaman et al. | 424/443 |
| 4,891,228 | 1/1990 | Thaman et al. | 424/443 |
| 4,942,029 | 7/1990 | Scheps | 424/78 |
| 4,971,784 | 11/1990 | Holzel et al. | 424/70 |
| 4,975,217 | 12/1990 | Brown-Skrobot et al. | 252/107 |
| 5,143,720 | 9/1992 | Lopes | 424/55 |
| 5,219,887 | 6/1993 | Andrews et al. | 514/552 |
| 5,234,719 | 8/1993 | Richter et al. | 427/384 |
| 5,280,042 | 1/1994 | Lopes | 514/557 |
| 5,380,756 | 1/1995 | Andrews et al. | 514/552 |
| 5,389,676 | 2/1995 | Michaels | 514/556 |
| 5,441,742 | 8/1995 | Autant et al. | 424/405 |
| 5,480,633 | 1/1996 | Simion et al. | 424/70.1 |
| 5,512,200 | 4/1996 | Garcia | 252/142 |
| 5,547,988 | 8/1996 | Yu et al. | 514/557 |
| 5,595,984 | 1/1997 | Blank | 514/159 |
| 5,607,980 | 3/1997 | McAtee | 514/476 |
| 5,620,694 | 4/1997 | Girardot | 424/402 |
| 5,629,081 | 5/1997 | Richards et al. | 442/96 |
| 5,631,218 | 5/1997 | Allan et al. | 510/423 |
| 5,635,462 | 6/1997 | Fendler et al. | 510/131 |
| 5,681,802 | 10/1997 | Fujiwara et al. | 510/130 |
| 5,700,842 | 12/1997 | Cole | 514/721 |
| 5,744,149 | 4/1998 | Girardot | 424/402 |
| 5,780,020 | 7/1998 | Peterson et al. | 424/65 |
| 5,972,361 | 10/1999 | Fowler et al. | 424/402 |
| 5,980,931 | 11/1999 | Fowler et al. | 424/443 |
| 6,063,397 | 5/2000 | Fowler et al. | 424/443 |

OTHER PUBLICATIONS

U.S. application No. 08/738,145, Fowler, filed Oct. 25, 1996.

U.S. application No. 08/740,280, Fowler et al., filed Oct. 25, 1996.

U.S. application No. 08/738,131 Fowler et al., filed Oct. 25, 1996.

Fowler et al, U.S. Patent Application Serial No. 09/065,991 claims abandoned.

U.S. application No. 08/959,969, R. W. Glenn et al., filed Oct. 24, 1997.

U.S. application No. 08/868,783 P. W. Beerse et al., filed Jun. 4, 1997.

U.S application No. 08/969,049, P. W. Beerse et al., filed Nov. 12, 1997.

U.S. application No. 08/868,982, P. W. Beerse et al., filed Jun. 4, 1997.

U.S. application No. 08/869,302, P. W. Beerse et al., filed Jun. 4, 1997.

U.S. application No. 08/869,300, P. W. Beerse et al., filed Jun. 4, 1997.

U.S. application No. 08/869,071, P. W. Beerse et al., filed Jun. 4, 1997.

U.S. application No. 08/869,688, P. W. Beerse et al., filed Jun. 4, 1997.

U.S. application No. 08/969,057, P. W. Beerse et al., filed Nov. 12, 1997.

U.S. application No. 08/868,687, P. W. Beerse et al., filed Jun. 4, 1997.

U. S. application No. 08/868,717, P. W. Beerse et al., filed Jun. 4, 1997.

U.S. application No. 08/869,301, P. W. Beerse et al., filed Jun. 4, 1997.

U.S. application No. 08/868,718, P. W. Beerse et al., filed Jun. 4, 1997.

U.S. application No. 08/967,972, P. W. Beerse et al., filed Nov. 12, 1997.

U.S. application No. 08/869,303, P. W. Beerse et al., filed Jun. 4, 1997.

U.S. application No. 08/869,129, P. W. Beerse et al., filed Jun. 4, 1997.

U.S. application No. 08/869,304, P. W. Beerse et al., filed Jun. 4, 1997.

U.S. application No. 08/869,117, P. W. Beerse et al., filed Jun. 4, 1997.

Ananthapadmanabhan, K.P., Yu, K.K., Meyers, C.L. and Aronson, M.P., Binding of Surfactants to Stratum Corneum, (1996),*J. Soc. Cosmet. Chem.,* vol. 47, pp. 185–200.

Antoine, J.L., Contreras, J.L. and Van Neste, D.J., pH Influence of Surfactant–induced Skin Irritation, (1989), *Dermatosen 37,* pp. 96–100.

Axe, Douglas D. and Bailey, JamesE., Transport of Lactate and Acetate Through the Energized Cytoplasmic Membrane of *Escherichia coli,* (1995),*Biotechnology and Bioengineering,* vol. 47, pp. 8–19.

Baker, Zelma, Ph.D., Harrison, R.W., and Miller, Benjamin F., M.D., Action of Synthetic Detergents on the Metabolism of Bacteria, (1940), *The Journal of Exp. Med.,* 73, pp. 249–271.

Bandelin, Fred J., The Effect of pH on the Efficiency of Various Mold Inhibiting Compounds, (1958), *The Journal of the American Pharmaceutical Association,* vol. XLVII, No. 10, pp. 96–98.

Bender, Max, Interfacial Phenomenia in Biological Systems, (1991),pp. 1–49.

Blank, Irvin H., PhD, Measurement of pH of the Skin Surface, (1939), *The Journal of Investigatvie Dermatology,* vol. 2, pp. 75–79.

Brown, M.R.W., The Role of the Cell Envelope in Resistance, *Resistance of Pseudomonas Aeruginosa,* pp. 70–107.

Buckley, D. and Thomas, J., Antimicrobial Activity of Sodium n–Alkylsalicylates, (1971),*Applied Microbiology,* vol. 21, No. 4, pp. 565–568.

Dychdala, G.R. and Lopes, John A., Surface–Active Agents: Acid–Anionic Compounds, *Disinfectants and Antiseptics: A. By Chemical Type,* pp.256–262.

Flexner, Simon, M.D., Rous, Peyton, M.D., Gasser, Herbert, M.D., The Journal of Experimental Medicine, (1941),V74, pp. 611–620.

Fukahori M., Akatsu S., Sato H., and Yotsuyanagi T., Relationship Between Uptake of p–hydroxybenzoic acid esters by *Escherichia coli* and Antibacterial Activity, (1996), Chem. Pharm. Bull., vol 44(8),pp.1567–1570.

Gershenfeld, Louis and Milanick, Vera Elaine, Bactericidal and Bacteriostatic Properties of Surface Tension Depressants, (1941), *American Journal of Pharmaceuticals,* 113, pp. 306–326.

Gershenfeld, Louis, D. Sc. and Perlstein, David, M. Sc., Significance of Hydrogen–ion Concentration in the Evaluation of the Bactericidal Efficiency of Surface Tension Depressants, (1941),*American Journal of Pharmaceuticals*, 113, pp. 89–92.

Gershenfeld, Louis and Witlin, Bernard, Surface Tension Reducents by Bactericidal Solutions: Their In Vitro and In Vivo Efficiencies, (1941), *American Journal of Pharmaceuticals*, 113, pp. 215–236.

Glassman, Harold N., Surface Active Agents and Their Application in Bacteriology, (1948),*Bacteriological Review*, V.13, pp.105–148.

Haque H. and A. D. Russell, Cell Envelopes of Gram Negative Bacteria: Compositions, Response to Chelating Agents and Suscpetibility of Whole Cells to Antibacterial Agents, J. Appl. Bact., (1976), vol. 40, pp. 89–99.

Hotchkiss, Rollin D., The Nature of the Bactericidal Actin of Surface Active Agents, *Annals New Academy of Sciences*, pp. 479–498.

Hubbard, A.W., Moore, L.J., Clothier, R.H., Sulley, H. and Rollin, K.A., Use of In Vitro Methodology to PRedict the Irritancy Potential of Surfactants, (1994), *Toxic. In Vitro*, vol. 8, No. 4, pp. 689–691.

Kabara, Jon J., Structure–function relationships of surfactants as antimicrobial agents, (1978), *Journal of the Society of Cosmetic Chemists*, 29, pp. 733–741.

Kostenbaueder, Harry B., Physical Factors Influencing the Activity of Antimicrobial Agents, pp. 59–71.

McDade, Joseph J. and Hall, Lawrence B., Survival of Gram–Negative Bacterial in the Environment, (1964), *Am. J. Hyg*, vol. 80, pp. 192–204.

Meincke, B.E., Kranz, R.G., Lynch, D.L., Effect of Irgasan on Bacterial Growth and Its Absorption Into the Cell Wall, (1980), *Microbios*, 28, pp. 133–147.

Ordal, E.J. and Deromedi, F., Studies on the Action of Wetting Agents on Microorganisms, (1943), *Journal of Applied Bacteriology 45*, pp. 293–299.

Rahn, Otto and Conn, Jean E., Effect of Increase in Acidity on Antiseptic Efficiency, (1994), *Industrial Engineering/Chemistry*, Soc. 36 (2) pp. 185–187.

Regos, J., Zak, O., Solf, R., Vischer, W.A. and Weirich, E.G., Antimicrobial Spectrum of Triclosan, a Broad–Spectrum Antimicrobial Agent for Topical Application, (1979), *Dermatologica 158*, pp. 72–29.

Russell, James B., Resistance of *Streptococcus bovis* to Acetic Acid at Low pH: Relationship between Intracellular pH and Anion Accumulation, (1991), *Applied and Environmental Microbiology*, vol. 57. No.1, pp. 255–259.

Russell, J.B., Another explanation for toxicity of fermentation acids at low pH: anion accumulation versus uncoupling, (1992), *Journal of Applied Bacteriology*, 73, pp. 363–370.

Scalzo, Marcello, Orlandi, Clelia, Simonetti, Nicola and Cerreto, Felice, Study of Interaction Effects of Polyacrylic Acid Polymers (Carbolpol 940) on Antimicrobial Activity of Methyl Parahyroxybenzoate Against Some Gram–negative, Gram–positive Bacteria and Yeast, (1996), *J. Pharm. Pharmacol*, pp. 1201–1205.

Schoenberg, Tom, Formulating Mild Body Washes, (1996), *happi*, pp. 53–56.

Sheena, A.Z. and Stiles, M.E., Immediate and Residual (Substantive) Efficacy of Germicidal Hand Wash Agents, (1983), *Journal of Food Protection*, vol. 46, No. 7, pp. 629–636.

Stotts, Jane, M.S. and Kooistra, John A., PhD., Micrococcaceae of Normal Human Skin Before and After Use of an Antibacterial Soap, (1970).

Wortzman, Mitchell S., PhD, Evaluation of Mild Skin Cleanser, (1991), *Dermatologic Clinics*, vol. 9, No. pp. 35–44.

Young, K.M. and Foegeding, Peggy M., Acetic, latic and citric acids and pH inhibition of *Listeria monocytogenes* Scott A and the Effect on Intracellular pH, (1993), *Journal of Applied Bacteriology*, 74, pp. 515–520.

Ciba Giegy Trade Literature: Basic Formaulation for Hand Disinfection 89/42/01, 89/42/05, & 91/01/49.

Head & Shoulders D Product: Finished Product Standard No. 8427 & 8428 dated Dec. 20, 1991.

Oil of Olay Age defying Series Daily Renewal Cleanser with Gentle Microbeads (Copy of Product).

LIQUID ANTIMICROBIAL CLEANSING COMPOSITIONS WHICH PROVIDE RESIDUAL BENEFIT VERSUS GRAM NEGATIVE BACTERIA

TECHNICAL FIELD

The present invention relates to mild, rinse-off, personal cleansing compositions which provide enhanced antimicrobial effectiveness. Specifically, the personal cleansing compositions of the invention provide previously unseen residual effectiveness against transient Gram negative bacteria.

BACKGROUND OF THE INVETION

Human health is impacted by many microbial entities. Inoculation by viruses and bacteria cause a wide variety of sicknesses and ailments. Media attention to cases of food poisoning, strep infections, and the like is increasing public awareness of microbial issues.

It is well known that the washing of hard surfaces, food (e.g. fruit or vegetables) and skin, especially the hands, with antimicrobial or non-medicated soap, can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria.

Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi.

Transient bacteria are bacteria which are not part of the normal resident flora of the skin, but can be deposited when airborne contaminated material lands on the skin or when contaminated material is brought into physical contact with it. Transient bacteria are typically divided into two subclasses: Gram positive and Gram negative. Gram positive bacteria include pathogens such as *Staphylococcus aureus*, *Streptococcus pyogenes* and *Clostridium botulinum*. Gram negative bacteria include pathogens such as Salmonella, *Escherichia coli*, Klebsiella, Haemophilus, *Pseudomonas aeruginosa*, Proteus and *Shigella dysenteriae*. Gram negative bacteria are generally distinguished from Gram positive by an additional protective cell membrane which generally results in the Gram negative bacteria being less susceptible to topical antibacterial actives.

Antimicrobial cleansing products have been marketed in a variety of forms for some time. Forms include deodorant soaps, hard surface cleaners, and surgical disinfectants. These traditional rinse-off antimicrobial products have been formulated to provide bacteria removal during washing. The antimicrobial soaps have also been shown to provide a residual effectiveness against Gram positive bacteria, but limited residual effectiveness versus Gram negative bacteria. By residual effectiveness it is meant that bacteria growth on a surface is controlled for some period of time following the washing/rinsing process. Antimicrobial liquid cleansers are disclosed in U.S. Pat. No. 4,847,072, Bissett et al., issued Jul. 11, 1989, U.S. Pat. No. 4,939,284, Degenhardt, issued Jul. 3, 1990 and U.S. Pat. No. 4,820,698, Degenhardt, issued Apr. 11, 1989, all of which are incorporated herein by reference.

Previously marketed formulations of Head & Shoulders® Dandruff Shampoo, marketed until 1994, comprised anionic surfactants, an antibacterial active and citric acid as a pH adjuster. Head & Shoulders® controlled *Pityrosorum ovale* fungus, which causes dandruff. PCT application WO 92/18100, Keegan et al., published Oct. 29, 1992 ("Keegan") and PCT application WO 95/32705, Fujiwara et al., published Dec. 7, 1995 ("Fujiwara") teach liquid skin cleansers comprising mild surfactants, antibacterial agents and acidic compounds to buffer the pH, which provide improved germ hostility. However, the use of the low levels of acid compounds therein, result in compositions which do not deliver the undissociated acid required to provide residual effectiveness versus Gram negative bacteria. This situation is compounded in Keegan and Fujiwara by the preference of mild surfactants, including nonionic surfactants.

Some of these antimicrobial products, especially the hard surface cleaners and surgical disinfectants, utilize high levels of alcohol and/or surfactants which have been shown to dry out and irritate skin tissues. Ideal personal cleansers should gently cleanse the skin, cause little or no irritation, and not leave the skin or hair overly dry after frequent use and preferably should provide a moisturizing benefit to the skin.

U.S. Pat. No. 3,141,821, issued to Compeau Jul. 21, 1964 and Irgasan DP 300 (Triclosan®) technical literature from Ciba-Giegy, Inc., "Basic Formulation for Hand Disinfection 89/42/01" set forth antibacterial skin cleansers compositions which could provide residual effectiveness versus Gram negative bacteria using certain anionic surfactants, antimicrobial actives and acids. However, the selection, therein, of highly active surfactants results in personal cleansing compositions which are drying and harsh to the skin.

Given the severe health impacts of Gram negative bacteria like Salmonella, *Escherichia coli* and Shigella, it would be highly desirable to formulate antimicrobial cleansing compositions which provide residual effectiveness versus these Gram negative bacteria and which are mild to the skin. Existing consumer products have been unable to achieve both Gram negative residual effectiveness and mildness.

Applicants have found that rinse-off antimicrobial cleansing compositions which provide such mildness and such residual effectiveness versus Gram negative bacteria can be formulated by using known antimicrobial actives in combination with specific organic and/or inorganic acids as proton donating agents, and specific anionic surfactants, all of which are deposited on the skin. The deposited proton donating agent and anionic surfactant enhance the selected active, to provide a new level of hostility to bacteria contacting the skin.

SUMMARY OF THE INVETION

The present invention relates to a rinse-off antimicrobial cleansing composition comprising from about 0.001% to about 5% of an antimicrobial active; from about 1% to about 80% of an anionic surfactant; from about 0.1% to about 12% of a proton donating agent; from about 0.1% to about 30% of a deposition aid; and from about 3% to about 98.8% of water. The compositions of the present invention have a pH of from about 3.0 to about 6.0. The rinse-off antimicrobial cleansing compositions further have a Gram Negative Residual Effectiveness Index of greater than about 0.3; and a Mildness Index of greater than 0.3.

The present invention also relates to methods for cleansing and for decreasing the spread of transient Gram negative bacteria using the rinse-off antimicrobial cleansing compositions described herein.

DETAILED DESCRIPTION OF THE INVENTION

The rinse-off antimicrobial cleansing compositions of the present invention are highly efficacious for cleansing surfaces, especially the skin, provide a residual antimicrobial effectiveness versus transient Gram negative bacteria and are mild to the skin.

The term "rinse-off" is used herein to mean that the compositions of the present invention are used in a context whereby the composition is ultimately rinsed or washed from the treated surface, (e.g. skin or hard surfaces) either after or during the application of the product.

The term "antimicrobial cleansing composition" as used herein means a composition suitable for application to a surface for the purpose of removing dirt, oil and the like which additionally controls the growth and viability of transient Gram negative bacteria. Preferred embodiments of the present invention are cleansing compositions suitable for use on the human skin.

The compositions of the present invention can also be useful for treatment of acne. As used herein "treating acne" means preventing, retarding and/or arresting the process of acne formation in mammalian skin.

The compositions of the invention can also potentially be useful for providing an essentially immediate (i.e., acute) visual improvement in skin appearance following application of the composition to the skin. More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin.

Regulating skin condition includes prophylactically and/or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign).

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

I. INGREDIENTS

The rinse-off antimicrobial cleansing compositions of the present invention comprise an antimicrobial active, an anionic surfactant, a proton donating agent, and a deposition aid. These components are selected so that the efficacy and mildness requirements hereinafter defined for the compositions herein are met. The selection of each component is necessarily dependent on the selection of each of the other components. For example, if a weak acid is selected as the proton donating agent, then in order to realize an efficacious composition, either a more biologically active (but possibly less mild) surfactant must be employed, and/or a high level of acid within the prescribed range must be used and/or a particularly efficacious active must be employed and/or a higher level of deposition aid within the prescribed range must be employed. Similarly, if a mild, but nonefficacious surfactant is employed, then a stronger acid and/or a high level of acid and/or a high level of deposition aid may be necessary to realize an efficacious composition. If a harsh surfactant is utilized, then a mildness agent may have to be utilized or a lipophilic skin moisturizer ingredient may have to be employed as the deposition aid. Guidelines for the selection of the individual components are provided herein.

A. ANTIMICROBIAL ACTIVE

The rinse-off antimicrobial cleansing compositions of the present invention comprise from about 0.001% to about 5%, preferably from about 0.01% to about 2%, more preferably from about 0.05% to about 1.5% and most preferably from about 0.1% to about 1.0% of an antimicrobial active. The exact amount of antibacterial active to be used in the compositions will depend on the particular active utilized since actives vary in potency. Non-cationic actives are required in order to avoid interaction with the anionic surfactants of the invention.

Given below are examples of non-cationic antimicrobial agents which are useful in the present invention.

Pyrithiones, especially the zinc complex (ZPT)
Octopirox®
Dimethyldimethylol Hydantoin (Glydant®)
Methylchloroisothiazolinone/methylisothiazolinone (Kathon CG®)
Sodium Sulfite
Sodium Bisulfite
Imidazolidinyl Urea (Germall 115®)
Diazolidinyl Urea (Germall II®)
Benzyl Alcohol
2-Bromo-2-nitropropane-1,3-diol (Bronopol®)
Formalin (formaldehyde)

Iodopropenyl Butylcarbamate (Polyphase P100®)
Chloroacetamide
Methanamine
Methyldibromonitrile Glutaronitrile (1,2-Dibromo-2,4-dicyanobutane or Tektamer®)
Glutaraldehyde
5-bromo-5-nitro-1,3-dioxane (Bronidox®)
Phenethyl Alcohol
o-Phenylphenol/sodium o-phenylphenol
Sodium Hydroxymethylglycinate (Suttocide A®)
Polymethoxy Bicyclic Oxazolidine (Nuosept C®)
Dimethoxane
Thimersal
Dichlorobenzyl Alcohol
Captan
Chlorphenenesin
Dichlorophene
Chlorbutanol
Glyceryl Laurate
Halogenated Diphenyl Ethers
    2,4,4'-trichloro-2'-hydroxy-diphenyl ether (Triclosan® or TCS)
    2,2'-dihydroxy-5,5'-dibromo-diphenyl ether
Phenolic Compounds
    Phenol
    2-Methyl Phenol
    3-Methyl Phenol
    4-Methyl Phenol
    4-Ethyl Phenol
    2,4-Dimethyl Phenol
    2,5-Dimethyl Phenol
    3,4-Dimethyl Phenol
    2,6-Dimethyl Phenol
    4-n-Propyl Phenol
    4-n-Butyl Phenol
    4-n-Amyl Phenol
    4-tert-Amyl Phenol
    4-n-Hexyl Phenol
    4-n-Heptyl Phenol
Mono- and Poly-Alkyl and Aromatic Halophenols
    p-Chlorophenol
    Methyl p-Chlorophenol
    Ethyl p-Chlorophenol
    n-Propyl p-Chlorophenol
    n-Butyl p-Chlorophenol
    n-Amyl p-Chlorophenol
    sec-Amyl p-Chlorophenol
    n-Hexyl p-Chlorophenol
    Cyclohexyl p-Chlorophenol
    n-Heptyl p-Chlorophenol
    n-Octyl p-Chlorophenol
    o-Chlorophenol
    Methyl o-Chlorophenol
    Ethyl o-Chlorophenol
    n-Propyl o-Chlorophenol
    n-Butyl o-Chlorophenol
    n-Amyl o-Chlorophenol
    tert-Amyl o-Chlorophenol
    n-Hexyl o-Chlorophenol
    n-Heptyl o-Chlorophenol
    o-Benzyl p-Chlorophenol
    o-Benxyl-m-methyl p-Chlorophenol
    o-Benzyl-m, m-dimethyl p-Chlorophenol
    o-Phenylethyl p-Chlorophenol
    o-Phenylethyl-m-methyl p-Chlorophenol
    3-Methyl p-Chlorophenol
    3,5-Dimethyl p-Chlorophenol
    6-Ethyl-3-methyl p-Chlorophenol
    6-n-Propyl-3-methyl p-Chlorophenol
    6-iso-Propyl-3-methyl p-Chlorophenol
    2-Ethyl-3,5-dimethyl p-Chlorophenol
    6-sec-Butyl-3-methyl p-Chlorophenol
    2-iso-Propyl-3,5-dimethyl p-Chlorophenol
    6-Diethylmethyl-3-methyl p-Chlorophenol
    6-iso-Propyl-2-ethyl-3-methyl p-Chlorophenol
    2-sec-Amyl-3,5-dimethyl p-Chlorophenol
    2-Diethylmethyl-3,5-dimethyl p-Chlorophenol
    6-sec-Octyl-3-methyl p-Chlorophenol
    p-Chloro-m-cresol
    p-Bromophenol
    Methyl p-Bromophenol
    Ethyl p-Bromophenol
    n-Propyl p-Bromophenol
    n-Butyl p-Bromophenol
    n-Amyl p-Bromophenol
    sec-Amyl p-Bromophenol
    n-Hexyl p-Bromophenol
    Cyclohexyl p-Bromophenol
    o-Bromophenol
    tert-Amyl o-Bromophenol
    n-Hexyl o-Bromophenol
    n-Propyl-m,m-Dimethyl o-Bromophenol
    2-Phenyl Phenol
    4-Chloro-2-methyl phenol
    4-Chloro-3-methyl phenol
    4-Chloro-3,5-dimethyl phenol
    2,4-Dichloro-3,5-dimethylphenol
    3,4,5,6-Terabromo-2-methylphenol
    5-Methyl-2-pentylphenol
    4-Isopropyl-3-methylphenol
    Para-chloro-meta-xylenol (PCMX)
    Chlorothymol
    Phenoxyethanol
    Phenoxyisopropanol
    5-Chloro-2-hydroxydiphenylmethane
Resorcinol and its Derivatives
    Resorcinol
    Methyl Resorcinol
    Ethyl Resorcinol
    n-Propyl Resorcinol
    n-Butyl Resorcinol
    n-Amyl Resorcinol
    n-Hexyl Resorcinol
    n-Heptyl Resorcinol
    n-Octyl Resorcinol
    n-Nonyl Resorcinol
    Phenyl Resorcinol
    Benzyl Resorcinol
    Phenylethyl Resorcinol
    Phenylpropyl Resorcinol
    p-Chlorobenzyl Resorcinol
    5-Chloro 2,4-Dihydroxydiphenyl Methane
    4'-Chloro 2,4-Dihydroxydiphenyl Methane
    5-Bromo 2,4-Dihydroxydiphenyl Methane
    4'-Bromo 2,4-Dihydroxydiphenyl Methane
Bisphenolic Compounds
    2,2'-Methylene bis (4-chlorophenol)
    2,2'-Methylene bis (3,4,6-trichlorophenol)
    2,2'-Methylene bis (4-chloro-6-bromophenol)
    bis (2-hydroxy-3,5-dichlorophenyl) sulphide
    bis (2-hydroxy-5-chlorobenzyl)sulphide
Benzoic Esters (Parabens)
    Methylparaben
    Propylparaben Butylparaben
Ethylparaben
Isopropylparaben
Isobutylparaben
Benzylparaben
Sodium Methylparaben
Sodium Propylparaben
Halogenated Carbanilides
  3,4,4'-Trichlorocarbanilides (Triclocarban® or TCC)
  3-Trifluoromethyl-4,4'-dichlorocarbanilide
  3,3',4-Trichlorocarbanilide Another class of antibacterial agents, which are useful in the present invention, are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae,* Ratanhiae and *Curcuma longa*. Also included in this class of natural essential oils are the key chemical components of the plant oils which have been found to provide the antimicrobial benefit. These chemicals include, but are not limited to anethol, catechole, camphene, thymol, eugenol, eucalyptol, ferulic acid, farnesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Additional active agents are antibacterial metal salts. This class generally includes salts of metals in groups 3b–7b, 8 and 3a–5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

Preferred antimicrobial agents for use herein are the broad spectrum actives selected from the group consisting of Triclosan®, Triclocarban®, Octopirox®, PCMX, ZPT, natural essential oils and their key ingredients, and mixtures thereof. The most preferred antimicrobial active for use in the present invention is Triclosan®.

B. ANIONIC SURFACTANT

Liquid embodiments of the rinse-off antimicrobial cleansing compositions of the present invention comprise from about 1% to about 80%, preferably from about 3% to about 50%, and more preferably from about 5% to about 25%, based on the weight of the personal cleansing composition, of an anionic surfactant. Solid bar embodiments of the present invention preferably comprise from about 10% to about 70%, and more preferably from about 20% to about 60% of the anionic surfactant. Without being limited by theory, it is believed that the anionic surfactant disrupts the lipid in the cell membrane of the bacteria. The particular acid used herein reduces the negative charges on the cell wall of the bacteria, crosses through the cell membrane, weakened by the surfactant, and acidifies the cytoplasm of the bacteria. The antimicrobial active can then pass more easily through the weakened cell wall, and more efficiently poison the bacteria.

Nonlimiting examples of anionic lathering surfactants useful in the compositions of the present invention are disclosed in McCutcheon's, *Detergents and Emulsifiers,* North American edition (1990), published by The Manufacturing Confectioner Publishing Co.; McCutcheon's, *Functional Materials,* North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention.

Anionic surfactants for use in the cleansing compositions include alkyl and alkyl ether sulfates. These materials have the respective formulae $R^1O$—$SO_3M$ and $R^1(CH_2H_4O)_x$—$O$—$SO_3M$, wherein $R^1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the cleanser compositions are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R^1CO$—$O$—$CH_2$—$C(OH)H$—$CH_2$—$O$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R^1\ SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium $C_{14}$–$C_{16}$ alpha olefin sulfonate.

Other suitable anionic surfactants are the linear alkylbenzene sulfonates of the form $R^1$—$C_6H_4$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing composition include the primary or secondary alkane sulfonates of the form $R^1 SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium $C_{13}$–$C_7$ paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable for use in the cleansing composition are the acyl isethionates. The acyl isethionates typically have the formula $R^1CO$—$O$—$CH_2CH_2SO_3M$ wherein $R^1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R^1$—$OCH_2$—$C(OH)H$—$CH_2$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R^1$—$CH(SO_4)$—$COOH$ and sulfonated methyl esters of the from $R^1$—$CH(SO_4)$—$CO$—$O$—$CH_3$, where $R^1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula $R^1CO$—$N(COOH)$—$CH_2CH_2$—$CO_2M$ wherein $R^1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula $R^1CON(CH_3)$—$CH_2CH_2$—$CO_2M$ wherein $R^1$ is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula $R^1$—$(OCH_2CH_2)_x$—$OCH_2$—$CO_2M$ wherein $R^1$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula $R^1CO$—$[O$—$CH(CH_3)$—$CO]_x$—$CO_2M$ wherein $R^1$ is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Any counter cation, M, can be used on the anionic surfactant. Preferably the counter cation is selected from the group consisting of sodium, potassium, ammonium, monoethanolamine, diethanolamine, and triethanolamine. More preferably the counter cation is ammonium.

Three factors must be taken into account when selecting the surfactant or surfactants to be employed in the antibacterial cleansing compositions herein: 1) the activity of the surfactant molecule at the cell membrane of the bacteria; 2) the solubility characteristics of the selected active in the surfactant, and 3) the mildness of the surfactant insofar as it affects the Mildness Index (hereinafter described) for the antimicrobial composition.

Biological Activity/Mildness of Surfactant

In general, the higher the biological activity of the surfactant, the more residual effectiveness is provided by the composition comprising the surfactant. Typically, however, the biological activity of a surfactant and the mildness of a surfactant are inversely proportional; the higher the biological activity of the surfactant, the harsher the surfactant and the lower the biological activity of the surfactant, the milder the surfactant. Whether a biologically active, but harsh surfactant or a mild, but biologically inactive surfactant is desired will, of course, depend on (or influence) the selection of the other components.

The biological activity/mildness of a pure surfactant can measured directly via a Microtox Response Test hereinafter described in the Analytical Methods section and can be reported as a Microtox Response Index. By "pure surfactant" it is meant a chemical composition consisting essentially of a single surfactant entity, wherein the entity has essentially one chain length, head group and salt counter ion. From a standpoint of high biological activity, preferred anionic surfactants of the antimicrobial cleansing compositions of the present invention have a Microtox Response Index of less that about 150, more preferably less than about 100 and most preferably less than about 50. From a standpoint of mildness, preferred anionic surfactants of the antimicrobial cleansing compositions of the present invention have a Microtox Response Index of greater than about 25, more preferably greater than about 50 and most preferably greater than about 100. Surfactants with a Microtox Response Index ranging from about 25 to about 150 are typically moderately biologically active and moderately mild.

For surfactant compositions which are mixtures of surfactants rather than pure surfactants (this includes "commercial grade" surfactants which typically comprise mixtures of entities with different chain lengths and potentially have higher levels of impurities), the Microtox Response Index for any individual surfactant component is not a reliable measurement of biological activity or mildness. In the case of mixtures, the Microtox Index of each individual component can be determined and the weighted average used as the Index for the mixture if all the individual components of the mixture are known. If the individual components of a mixture are not known, then the head group and chain lengths of the surfactant mixture is a better indicator of biological activity/mildness.

Anionic surfactants or mixtures of surfactants with a chain length primarily in the range of from about 8 to about 24 carbon atoms, preferably primarily from about 10 to about 18 carbon atoms and most preferably primarily from about 12 to about 16 carbon atoms are preferred from the standpoint of high biological activity. As used herein "primarily" means at least about 50%. From a standpoint of mildness, it is preferable to minimize C12.

From the standpoint of biological activity, it is preferred that the head group of the anionic surfactant be less than about 15 Angstroms, preferably less than about 10 Angstoms, and more preferably less than about 7 Angstoms. The "head group" is defined as the hydrophilic portion (non-hydrocarbon) of the anionic surfactant, measured from the first polar atom to the end of the molecule. The head group size is estimated from the Van der Waals radius of the atoms and the configuration of the surfactant molecule. Head groups with sizes less than about 7 Angstroms include sulfates, sulfonates, and phosphates. From the standpoint of mildness, it is preferred that the head group size is greater than about 7 Angstoms, and preferably greater than about 10 Angstoms. Head groups with sizes greater than about 10 Angstroms include ethoxylated sulfates, glyceryl ether sulfonates, and isethionates. It is believed that as the head group size increases, more stearic hindrance at the cell wall prevents disruption by the surfactant and, thus, biological activity is decreased and mildness is increased.

The mildness of a surfactant or mixture of surfactants can also be determined by a number of other known, conventional methods for measuring surfactant mildness. For example, the Barrier Destruction Test set forth in T. J. Franz, *J. Invest. Dermatol.*, 1975, 64, pp. 190–195 and in U.S. Pat. No. 4,673,525 to Small et al; issued Jun. 16, 1987, both of which are herein incorporated by reference, is a way of measuring mildness of surfactants. In general, the milder the surfactant, the less skin barrier that is destroyed in the barrier destruction test. Skin barrier destruction is measured by relative amount of radiolabeled water which passes from the test solution through the skin epidermis into the physiological buffer contained in the diffusate chamber. Surfactants having a Relative Skin Barrier Penetration Value of as close to zero as possible up to about 75 are considered mild for purposes herein. Surfactants having a Relative Skin Barrier Penetration Value of greater than about 75 are considered harsh for purposes herein.

Solubility slope of Antimicrobial Active in Anionic Surfactant

Preferred anionic surfactants are also selected, in part, based on the ability of the surfactant to deposit the antimicrobial active onto the skin. Surfactants for use herein must have sufficient solubility to carry the active and yet the solubility cannot be so high that the active is held in solution during use, resulting in no active being deposited to the skin. It has been found that this balance is best measured by the slope of the curve of the solubility of the antimicrobial active versus the concentration of the surfactant in water. This slope, hereafter referred to as the solubility slope, K, is determined by the test method hereinafter described in the Analytical Methods Section.

Preferred anionic surfactants of the present invention comprise a solubility slope, K, of less than 0.60, preferably less than 0.40, more preferably less than about 0.25 and most preferably less than about 0.10.

The rinse-off antimicrobial cleansing compositions of the present invention preferably deposit from about 0.01 $\mu g/cm^2$ to about 100 $\mu g/cm^2$, more preferably from about 0.1 $\mu g/cm^2$ to about 50 $\mu g/cm^2$ and most preferably from about 1 $\mu g/cm^2$ to about 20 $\mu g/cm^2$ of antimicrobial active onto the skin.

In order for the personal cleansing compositions herein to be effective, both the biological activity of the surfactant and the solubility of the particular active employed in the surfactant must be taken into account.

For example, ammonium lauryl sulfate, ALS, is very biologically active (Microtox Index=1.0) but has a relatively high solubility slope (K=0.3). Compositions comprising ALS are capable of providing very effective residual antibacterial effectiveness due to its activity, even with lower levels of antibacterial active and proton donating agent. However, in order to deposit the active on the skin (which is required to meet the efficacy requirements described herein), higher levels of active will be required as a result of the high solubility slope. Moreover, compositions containing ALS may require the addition of co-surfactants or polymers, described herein in the Optional Ingredient Section, to achieve most preferred mildness levels for the present invention.

A selection of ammonium laureth sulfate (Microtox=120 and K=0.5) as a surfactant will result in compositions which are very mild, but which would require higher levels of proton donating agent and antimicrobial active in order to achieve the residual effectiveness of the present invention.

Paraffin sulfonate, a commercial grade surfactant sold under the name Hastapur SAS® from Hoechst Celanese, with a small head group and average chain length of 15.5 (K=0.1) is a relatively active surfactant and provides very high deposition of the active. Compositions comprising lower levels of active and acid can be used with higher levels of paraffin sulfonate, where the surfactant provides a larger component of residual effectiveness. Alternately, compositions comprising lower levels of paraffin sulfonate can be combined with even higher levels of active to achieve a mild and effective composition. Moderate levels of active can be used with paraffin sulfonate, since its solubility index indicates that such compositions will have very high deposition of the active.

Nonlimiting examples of preferred anionic surfactants useful herein include those selected from the group consisting of sodium and ammonium alkyl sulfates and ether sulfates having chain lengths of predominantly 12 and 14 carbon atoms, olefin sulfates having chain lengths of predominantly 14 and 16 carbon atoms, and paraffin sulfonates having chain lengths of from 13 to 17 carbon atoms, and mixtures thereof. Especially preferred for use herein is ammonium and sodium lauryl sulfate; ammonium and sodium myristyl sulfate; ammonium and sodium laureth-1, laureth-2, laureth-3, and laureth-4 sulfate; ammonium and sodium, C14–C16 olefin sulfonates; C13–C17 paraffin sulfonates, and mixtures thereof.

Non-anionic surfactants of the group consisting of non-ionic surfactants, cationic surfactants, amphoteric surfactants and mixtures thereof, have been found to actually reduce residual effectiveness benefits when used with anionic surfactants at high levels. This is most evident in the case of cationic and amphoteric surfactants where it is believed that these surfactants interfere (charge-charge interaction) with the anionic surfactant's ability to disrupt of the lipid in the cell membrane. The ratio of the amount of these non-anionic surfactants to the amount of anionic surfactant should be less than 1:1, preferably less than about 1:2, and more preferably less than about 1:4.

The rinse-off antimicrobial cleansing compositions of the present invention preferably do not comprise hydrotropic sulfonates, particularly salts of terpenoids, or mono- or binuclear aromatic compounds such as sulfonates of camphor, toluene, xylene, cumene and naphthene.

C. PROTON DONATING AGENT

The rinse-off antimicrobial cleansing compositions of the present invention comprise from about 0.1% to about 12%, preferably from about 0.5% to about 10%, more preferably from about 1% to about 7.5%, and most preferably from about 2.5% to about 5%, based on the weight of the personal cleansing composition, of a proton donating agent. By "proton donating agent" it is meant any acid compound or mixture thereof, which results in the presence of undissociated acid on the skin after use. Proton donating agents can be organic acids, including polymeric acids, mineral acids or mixtures thereof.

Organic Acids

Proton donating agents which are organic acids remain at least partially undissociated in the neat composition and remain so when the compositions are diluted during washing and rinsing. The organic acid proton donating agent must have at least one pKa value below 5.5. These organic proton donating agents can be added directly to the composition in the acid form or can be formed by adding the conjugate base of the desired acid and a sufficient amount of a separate acid strong enough to form the undissociated acid from the base.

Biological Activity Index of Organic Acids

Preferred organic proton donating agents are selected based on their biological activity. This activity is represented by a Biological Activity Index, Z, which is defined as:

$$Z=1+0.25pKa_1+0.42logP.$$

The biological activity index combines the dissociation characteristics and the hydrophobicity of the acid. It is critical that the undissociated proton donating agent of the composition be deposited on the skin to reduce the negative charge on the cell wall. The acid's dissociation constant, $pKa_1$, is indicative of the chemical's proton donating capacity relative to the pH of the medium in which it is incorporated. Since more undissociated acid is preferable in the composition, acids with higher pKa's are generally more preferred for a given product pH. The octanol-water partition coefficient, P, represents the tendency of materials in solution to prefer either oils or water. It essentially is a measure of hydrophobic nature of a material in solution: the higher the partition coefficient, the more oil soluble, and less water soluble, the material. Since it is desired that the dissolved acids in the compositions come out of the aqueous cleanser upon application, deposit on the oil-based skin and remain during rinsing, organic acids with higher octanol-water partition coefficients are more preferred.

Preferred organic proton donating agents of the rinse-off antimicrobial cleansing compositions of the present invention have a biological activity index greater than about 0.5, preferably greater than about 1.0, more preferably greater than about 1.5 and most preferably greater than 2.0.

Mineral Acids

Proton donating agents which are mineral acids will not remain undissociated in the neat composition or when the compositions are diluted during washing and rinsing. Despite this, it has been found that mineral acids can be effective proton donating agents for use herein. Without being limited by theory, it is believed that the strong mineral acids, protonate the carboxylic and phosphatidyl groups in proteins of the skin cells, thereby providing in-situ undissociated acid. These proton donating agents can only be added directly to the composition in the acid form.

pH

It is critical to achieving the benefits of the invention that the undissociated acid from the proton donating agent (deposited or formed in-situ) remain on the skin in the protonated form. Therefore, the pH of the rinse-off antimicrobial cleansing compositions of the present invention must be adjusted to a sufficiently low level in order to either form or deposit substantial undissociated acid on the skin. The pH of the compositions should be adjusted and preferably buffered to have a range of from about 3.0 to about 6.0, preferably from about 3.0 to about 5.0 and more preferably from about 3.5 to about 4.5.

A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polymeric acids, their salts, and mixtures thereof. A non-exclusive list of examples of mineral acid for use herein are hydrochloric, phosphoric, sulfuric and mixtures thereof.

Polymeric acids are especially preferred acids for use herein from the standpoint that they cause less stinging to the skin than other acids, they can have less of a negative impact on lather than other acids and they can contribute to a draggy rinse feel which is preferred by some consumers. As used herein, the term "polymeric acid" refers to an acid with repeating units of carboxylic acid groups joined together into one chain. Suitable polymeric acids can include homopolymers, copolymers and terpolymers, but must contain at least 30 mole % carboxylic acid groups. Specific examples of suitable polymeric acids useful herein include poly(acrylic) acid and its copolymers, both ionic and nonionic, (e.g., maleic-acrylic, sulfonic-acrylic, and styrene-acrylic copolymers), those cross-linked polyacrylic acids having a molecular weight of less than about 250,000, preferably less than about 100,000 poly (α-hydroxy) acids, poly (methacrylic) acid, and naturally occurring polymeric acids such as carageenic acid, carboxy methyl cellulose, and alginic acid. Straight-chain poly(acrylic) acids are especially preferred for use herein.

D. DEPOSITION AID

The liquid, rinse-off antimicrobial personal cleansing compositions herein comprise from about 0.1% to about 30%, preferably from about 1% to about 30% more preferably from about 3% to about 25%, most preferably from about 5% to about 25% of a deposition aid. It has been found that compositions which contain a deposition aid have improved antibacterial efficacy compared to compositions which do not contain a deposition aid. The deposition aid employed herein is one that increases the deposition of the antimicrobial active or the proton donating agent on the skin by at least about 20%, preferably by at least about 30%, more preferably at least about 50%.

Suitable deposition aids for use herein include, for example, lipophilic skin moisturizing agents, cationic polymers, nonionic polymers, zeolites, clays and mixtures thereof. One of the reasons why cationic polymers are believed to be effective deposition aids is that they can form coascervates with the anionic surfactant.

Suitable cationic and nonionic polymers for use as a deposition aid herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When cationic or nonionic polymers are employed as the deposition aid, they are utilized at levels ranging from about 0.1% to about 1.0%, preferably from about 0.15% to about 0.8%, more preferably from about 0.2% to about 0.6% by weight of the composition. Lipophilic skin moisturizing agents are especially preferred as a deposition aid in the present invention. In addition to providing improved antibacterial efficacy compared to compositions which do not contain a deposition aid, the lipid skin moisturizing agent provides a moisturizing benefit to the user of the personal cleansing product when the lipophilic skin moisturizing agent is deposited to the user's skin. When lipophilic skin moisturizing agents are used as the deposition aid herein, they are employed at a level of about 1% to about 30%, preferably from about 3% to about 25%, most preferably from about 5% to about 25% by weight of the composition.

Two types of rheological parameters are used to define the lipophilic skin moisturizing agent used herein. The viscosity of the lipophilic skin moisturizing agent is represented by consistency (k) and shear index (n). The lipophilic skin moisturizing agents for use herein typically have a consistency (k) ranging from about 5 to about 5,000 poise, preferably from about 10 to about 3,000 poise, more preferably from about 50 to about 2,000 poise, as measured by the Consistency (k) Method hereinafter set forth in the Analytical Methods section. Suitable lipophilic skin moisturizing agents for use herein further have a shear index (n) ranging from about 0.01 to about 0.9, preferably from about 0.1 to about 0.5, more preferably from about 0.2 to about 0.5, as measured by the Shear Index Method hereinafter set forth in the Analytical methods section.

While not being bound by any theory, it is believed that lipophilic skin moisturizing agents having rheology properties other than those defined herein are either too easily emulsified and hence will not deposit, or are too "stiff" to adhere or deposit on to skin and provide a moisturization benefit. In addition, the rheological properties of the lipophilic skin moisturizing agent are also important to user perception. Some lipophilic skin moisturizing agents, on deposition to the skin, are considered too sticky and are not preferred by the user.

In some cases, the lipophilic skin moisturizing agent can also desirably be defined in terms of its solubility parameter, as defined by *Vaughan in Cosmetics and Toiletries,* Vol. 103, p. 47–69, Oct. 1988. A lipophilic skin moisturizing agent having a Vaughan solubility Parameter (VSP) from 5 to 10, preferably from 5.5 to 9 is suitable for use in the liquid personal cleansing compositions herein.

A wide variety of lipid type materials and mixtures of materials are suitable for use as the carrier in the antimicrobial personal cleansing compositions of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797, 300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil micro-crystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di- and tri-plycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid nondigestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, microcrystalline wax, polyalkene, paraffin, cerasin, ozokerite, polyethylene, perhydrosqualene, dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

E. WATER

Liquid rinse-off antimicrobial cleansing compositions of the present invention comprise from about 35% to about 98.8%, preferably from about 45% to about 98%, more preferably from about 55% to about 97.5%, and most preferably from about 65% to about 95.99% water. Solid bar embodiments of the present invention preferably comprise from about 2% to about 25%, more preferably from about 3% to about 20% and most preferably from about 5% to about 15% water.

Liquid rinse-off antimicrobial cleansing compositions of the present invention, preferably have an apparent or neat viscosity of from about 500 cps to about 60,000 cps at 26.7° C., preferably 5,000 to 30,000 cps. The term "viscosity" as used herein means the viscosity as measured by a Brookfield RVTDCP with a spindle CP-41 at 1 RPM for 3 minutes, unless otherwise specified. The "neat" viscosity is the viscosity of the undiluted liquid cleanser.

F. PREFERRED OPTIONAL INGREDIENTS

Mildness Enhancers

In order to achieve the mildness required of the present invention, optional ingredients to enhance the mildness to the skin can be added. These ingredients include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1.0%, and more preferably from about 0.2% to about 0.6%, by weight of the rinse-off antimicrobial cleansing composition, of the composition. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the co-solvents comprise from about 20% to about 70%, preferably from about 20% to about 50%, by weight of the anionic surfactant, of the cleansing composition.

Stabilizers

When a lipophilic skin moisturizing agent is employed as the deposition aid in the liquid antimicrobial compositions herein, a stabilizer is also included at a level ranging from about 0.1% to about 10%, preferably from about 0.1% to about 8%, more preferably from about 0.1% to about 5% by weight of the composition.

The stabilizer is used to form a crystalline stabilizing network in the liquid cleansing composition that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability, but allow the liquid personal cleansing composition to separate upon lathering, and thereby provide for increased deposition of the lipophilic skin moisturizing agent onto the skin. This is particularly true when the cleansing emulsions of the present invention are used in conjunction with a polymeric diamond meshed sponge implement such as that described in Campagnoli; U.S. Pat. No. 5,144,744; Issued Sep. 8, 1992, herein incorporated by reference.

In one embodiment of the present invention, the stabilizer employed in the personal cleansing compositions herein comprises a crystalline, hydroxyl-containing stabilizer. This stabilizer can be a hydroxyl-containing fatty acid, fatty ester or fatty soap water-insoluble wax-like substance or the like.

The crystalline, hydroxy-containing stabilizer is selected from the group consisting of:

(i)

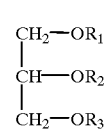

wherein $R_1$ is

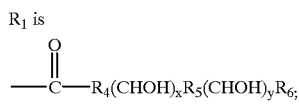

$R_2$ is $R_1$ or H $R_3$ is $R_1$ or H $R_4$ is $C_{0-20}$ Alkyl $R_5$ is $C_{0-20}$ Alkyl, $R_6$ is $C_{0-20}$ Alkyl $R_4 + R_5 + R_6 = C_{10-22}$ and wherein $1 \leq x+y \leq 4$;

(ii)

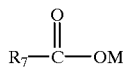

wherein $R_7$ is $-R_4(CHOH)_xR_5(CHOH)_yR_6$

M is $Na^+$, $K^+$ or $Mg^{++}$, or H; and iii) mixtures thereof;

Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.1% to 10%, preferably from 0.1% to 8%, more preferably from 0.1% to about 5% of the liquid personal cleansing compositions. The stabilizer is insoluble in water under ambient to near ambient conditions.

Alternatively, the stabilizer employed in the personal cleansing compositions herein can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic, cationic, and nonionic homopolymers derived from acrylic and/or methacrylic acid, anionic, cationic, and nonionic cellulose resins, cationic copolymers of dimethyldialkylammonium chloride, and acrylic acid, cationic homopolymers of dimethylalkylammonium chloride, cationic polyalklene and ethoxypolyalkylene imines, polyethylene glycol of molecular weight from 100,000 to 4,000,000, and mixtures thereof. Preferably, the polymer is selected from the group consisting of sodium polyacrylate, hydroxy ethyl cellulose, cetyl hydroxy ethyl cellulose, and Polyquaternium 10.

Alternatively, the stabilizer employed in the personal cleansing compositions herein can comprise C10–C22 ethylene glycol fatty acid esters. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the personal cleansing compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Dat Pamphlet TD-104 entitled "CAB-O-SILS Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from'about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the emulsion compositions at levels ranging from about 0.1% to about 10%, preferably from about 0.25% to about 8%, more preferably from about 0.5% to about 5%.

A fourth class of stabilizer which can be employed in the personal cleansing compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the personal cleansing compositions of the present invention, it is typically included in amounts ranging from about 0.1% to about 10%, preferably from about 0.25% to about 8%, more preferably from about 0.5% to about 5%.

Other known stabilizers, such as fatty acids and fatty alcohols, can also be employed in the compositions herein. Lauric and palmitic fatty acids are especially preferred stabilizers for use herein.

G. OTHER OPTIONAL INGREDIENTS

The compositions of the present invention can comprise a wide range of optional ingredients. The *CTFA International Cosmetic Ingredient Dictionary,* Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

II. CHARACTERISTICS

The rinse-off antimicrobial cleansing compositions herein, have the following characteristics.

A. GRAM NEGATIVE RESIDUAL EFFECTIVENESS INDEX

The rinse-off antimicrobial cleansing compositions of the present invention have a Gram Negative Residual Effectiveness Index of greater than about 0.3 (50% reduction), preferably greater.than about 1.0 (90% reduction), more preferably greater than about 1.3 (95% reduction), and most preferably greater than about 2.0 (99% reduction). The Gram Negative Residual Effectiveness Index is measured by the In-Vivo Residual Effectiveness on *Escherichia coli* Test described hereinafter in the Analytical Methods Section. The index represents a difference in base ten logarithm values of bacterial concentrations between a test sample and a control. For example, an index of 0.3 represents a reduction in log values of 0.3 ($\Delta\log=0.3$) which in turn represents a 50% reduction of bacteria counts.

B. MILDNESS INDEX

The rinse-off antimicrobial cleansing compositions of the present invention comprise a Mildness Index of greater than about 0.3, preferably greater than about 0.4, and more preferably greater than about 0.6. The Mildness Index is measured by the Forearm Controlled Application Test (FCAT) described hereinafter in the Analytical Methods Section.

III. METHODS OF MANUFACTURE OF RINSE-OFF ANTIMICROBIAL CLEANSING COMPOSITION

The rinse-off antimicrobial personal cleansing compositions of the present invention are made via art recognized techniques for the various forms of personal cleansing products.

IV. METHODS OF USING THE RINSE-OFF ANTIMICROBIAL CLEANSING COMPOSITION

The rinse-off antimicrobial personal cleansing compositions of the present invention are useful for personal cleansing, especially for cleansing of the hands. Typically, a suitable or effective amount of the cleansing composition is applied to the area to be cleansed. Alternatively, a suitable amount of the cleansing composition can be applied via intermediate application to a washcloth, sponge, pad, cotton ball, puff or other application device. If desired, the area to be cleansed can be premoistened with water. The compositions of the present invention are combined with water during the cleansing process and rinsed-off from the skin. Generally, an effective amount of product to be used will depend upon the needs and usage habits of the individual. Typical amounts of the present compositions useful for cleansing range from about 0.1 mg/cm$^2$ to about 10 mg/cm$^2$, preferably from about 0.6 mg/cm$^2$ to about 5 mg/cm$^2$ skin area to be cleansed.

ANALYTICAL TEST METHODS

MICROTOX RESPONSE TEST

Reference: *Microtox Manual: A Toxicity Testing Handbook.* 1992 Volume I–IV, Microbics Corporation.

Equipment: Microtox M500 Toxicity Testing Unit; Microbics Corporation Connected to computer for data acquisition and analysis according to above reference.

Procedure:

1. Preparation of Sample Stock Solution (Standard Concentration: 1000 )ppm)

The stock solution of the test anionic surfactant sample is prepared and used as a stock solution from which all other dilutions are made. The standard "starting concentration", the highest concentration to be tested, is 500 ppm. (If a 500 ppm starting concentration fails to give a calculable result, e.g. an active surfactant kills all reagent at all dilutions, the starting concentration can be adjusted based on a known range of EC50 values of previously tested surfactants.) The stock solution is prepared at two times the starting concentration.

a) Add 0.1 g (or adjusted amount if required) of anionic surfactant, accounting for activity of raw material, to beaker.

b) Microtox Diluent (2% NaCl, Microbics Corp.) is added to total 100g.

c) Stir solution to make sure of adequate mixing.

2. Reconstitution of Microtox Reagent and Preparation of Assay a) Turn on test unit and allow reagent well temperature to equilibrate at 5.5° C. and incubator block and read well temperature to equilibrate at 15° C.

b) Place a clean cuvette (Microbics Corp.) in the reagent well, and fill with 1.0 ml of Microtox Reconstitution Solution (distilled water, Microbics, Corp.). Allow to cool for 15 minutes.

c) Reconstitute standard vial of Microtox Acute Toxicity Reagent (*Vibrio fischerio,* Microbics Corp.) by quickly adding the 1.0 ml of the cooled reconstitution solution to the reagent vial.

d) Swirl solution in the reagent vial for 2–3 seconds then pour reconstituted reagent back into the cooled cuvette and return the vial to the reagent well. Allow to stabilize for 15 minutes.

e) Place 8 cuvettes containing 500 μl of Microtox Diluent, as assay, into the incubator wells of the test unit. Let cool for 15 minutes.

3. Test Substance Dilution

Prepare 7 serial dilutions of the test substance from the sample stock solution. The final volume of all cuvettes must be 1.0 ml.

a) Place 8 empty cuvettes into a test tube rack.

b) Add 1.0 ml of Microtox Diluent solution to tubes 1–7.

c) Add 2.0 ml of the sample stock solution (1000 ppm) in cuvette 8.

d) Transfer 1.0 ml solution from cuvette 8 to cuvette 7 and mix cuvette 7.

e) Serially transfer 1.0 ml from the newly formed solution to the subsequent cuvette (7 to 6, 6 to 5 etc.). Remove 1.0 ml of solution from cuvette 2 and discard. Cuvette 1 is the blank containing only Microtox Diluent. Place the cuvettes into the test unit incubation wells keeping them in order of lowest to highest concentration. These cuvettes should correspond with the 8 cuvettes prepared in step 2 above. Allow to cool for 15 minutes.

4. Assay and Sample Bioluminescence Testing a) Add 10 μl of reconstituted reagent to the 8 precooled cuvettes of assay prepared in step 2 above (containing 500 μl of diluent). Allow 15 minutes for reagent to stabilize.

b) Start Microtox Data Capture and Reporting Software (Microbics Corp.), select START TESTING, input file name and description, correct starting concentration in ppm (500 if standard concentration is used) and number of controls (1) and dilutions (7). Time 1 should be selected as 5 minutes, time 2 is NONE. Press enter then the space bar to begin testing.

c) Place the assay cuvette containing reagent which corresponds to the test blank into the read well and press SET. After the cuvette has resurfaced press READ and the value will be captured by the computer.

d) Similarly read the remaining 7 cuvettes containing reagent when prompted by the computer by pressing the READ button with the correct cuvette in the READ well.

e) After all 8 initial reading have been taken, transfer 500 μl of the diluted test substance into their corresponding cuvette containing the reagent. Mix by vortexing or swirling and return to the incubation wells. The computer will count for five minutes and prompt you to begin final readings.

f) Take final readings by placing the correct cuvette containing reagent and diluted test surfactant into the read well and pressing READ when prompted by the computer.

5. Data Analysis

The concentration of test substance, in ppm, that decreases the bioluminescence of the Microtox Acute Toxicity Reagent by 50% from the starting value (EC50 Value) can be calculated using the Run Statistics on Data File option of the Microtox Software (recommended) or by conducting a linear regression of the data (% reduction vs. log of concentration). % Reductions are calculated using the following formulas:

$$\frac{\text{Final Reading of Reagent Blank}}{\text{Initial Reading of Reagent Blank}} = \text{Correction Factor}$$

$$\frac{\text{Final Reading of Reagent with Diluted Test Substance}_x}{\text{Initial Reading of Reagent with Diluted Test Substance}_x} = \text{Reduction Factor}_x$$

where x means at a corresponding concentration $$\% \text{ Reduction} = \frac{\text{Correction Factor}_x - \text{Reduction Factor}}{\text{Correction Factor}}$$

The Microtox Index is the EC50 value in ppm.

SOLUBILITY SLOPE, K

Equipment: Liquid Scintillation Counter equipped with correct quench curve for liquid scintillation fluid used (Ultima Gold, Packard Instrument Co.)

1. Preparation of $^{14}C$ labeled Triclosan®
   a) Add 5.00 g of regular triclosan (TCS) powder to a 20 ml vial.
   b) Add 10 $\mu$Ci of $^{14}C$ TCS and 1 ml of acetone.
   c) Stir the solution for 3 minutes or until all TCS is dissolved.
   d) Blow in $N_2$ to remove most solvent until it solidifies again.
   e) Grind the solid to powder and dry it under $N_2$ overnight to yield the labeled material ready for use.
   f) Measure activity of TCS in DPM/g to use as conversion factor for later samples.
      1. Place about 0.1 g of powdered TCS (note weight) from step e above into liquid scintillation vial.
      2. Add 10 ml of liquid scintillation fluid (Ultima Gold).
      3. Place in liquid scintillation counter and count decays per minute (DPM) of sample.
      4. Divide DPM by TCS weight from step 1-f-1 to determine conversion factor (DPM/g TCS).

2. Solubility protocol
   a) Prepare stock solution of TCS deprived formula with anionic surfactant level of 16% in 7–9 grain tap water.
   b) Place 8 empty cuvettes into a test tube rack.
   c) Add 3 ml of the stock solution into a scintillation vial 1.
   d) Prepare five individual 3 ml solutions which are 1:2, 1:4, 1:8, 1:16, and 1:32 dilutions of the stock solution in five scintillation vials (ending concentrations are 8%, 4% 2%, 1%, and 0.5%).
   e) To each vial add about 0.05 g of the radio labeled TCS (from step 1-e above) and a magnetic stirring bar. Stir the vials as a group for at least 2 hours. If the TCS solid phase disappears, add additional TCS to ensure phase equilibrium.
   f) For each dilution, remove about 1.0 ml, place in 1.5 ml microcentrifuge tube, and centrifuge it for 5 minutes at 1500 RPM.
   g) Remove about 0.1–0.4 g (note weight) from top layer of centrifuged sample and place in a clean liquid scintillation vial.
   h) Add 10 ml of liquid scintillation cocktail (Ultima Gold) to the vial.
   i) Count the vial's DPM using the liquid scintillation counter.
   j) Covert DPM to TCS weight using conversion factor from step 1-f above.
   k) Calculate percentage TCS (maximum solubility in sample) by dividing by weight from step 2-g.
   l) Repeat g through 1 for each serial dilution of anionic surfactant.

3. Calculation of K

The Solubility Slope, K, is calculated by conducting a linear regression of maximum TCS solubility vs. surfactant concentration within the limits discussed below.

a) For almost all surfactants the slope of the solubility curve between 1 and 2% surfactant is representative of K.
   b) For some surfactants the maximum TCS solubility curve remains linear outside the 1–2% surfactant region. K must then be calculated from this entire linear region, such as from 0–4%, 1–4%, or 0.5–2% surfactant levels. It is important that K is calculated near the 2% surfactant range because this is an approximate concentration of surfactant in a diluted cleansing composition.

IN-VIVO RESIDUAL EFFECTIVENESS ON *E.coli*

References: Aly, R; Maibach, H. I.; Aust, L. B.; Corbin, N. C.; Finkey, M. B. 1994.

1. In vivo effect of antimicrobial soap bars containing 1.5% and 0.8% trichlorocarbanilide against two strains of pathogenic bacteria. J. Soc. Cosmet. Chem., 35, 351–355, 1981.

2. In vivo methods for testing topical antimicrobial agents. J. Soc. Cosmet. Chem., 32, 317–323.

1. Test Design

Residual Antibacterial efficacy of liquid and bar soap antimicrobial products are quantified in the following method. Reductions are reported from a control, non-antibacterial placebo soap, without further treatment, used on one of the subjects forearms. By definition the antibacterial placebo will show no residual effectiveness in the test.

2. Pre-Test Phase

Subjects are instructed not to use antibacterial products for 7 days prior to testing. Immediately before test, the subjects hands are examined for cuts/broken skin that would preclude them from participating.

3. Wash Procedure a) Wash both forearms with control soap one time to remove any contaminants or transient bacteria. Rinse and dry forearms
   b) Test monitor wets gloved hands, places 1.0 ml of liquid test product (bar treatments are done according to above references) on forearm of subject, and lathers entire volar forearm with hand for 45 sec.
   c) Subjects forearms are then rinsed with 90–100° F. tap water at a rate of 1 GPM for 15 seconds.
   d) Steps b–c are repeated two times (total 3 washes) for the test product.
   e) Arm is patted dry with paper towel and test sites are marked (~8.6 $cm^2$ circle with rubber stamp).
   f) This entire procedure (a–e) is repeated on other forearm of subject with control product.

4. Inoculation Procedure a) *E. coli* inoculum (ATCC 10536, grown from lyophilized stock in Soybean-casein broth at 37 C. for 18–24 hrs) is adjusted to approximately $10^8$ organisms/ml (0.45 transmittance vs. TSB blank on specrophotometer).

b) Each test site is inoculated with 10 µL of *E. coli*. Inoculum is spread with inoculating loop into a ~3 cm$^2$ circle and covered with a Hilltop Chamber (Hilltop Research Inc.).

c) This procedure is repeated for each test site on each forearm.

5. Sampling Bacteria (Extraction Procedure)

a) Prepare sampling solution of 0.04% $KH_2PO_4$, 1.01% $Na_2HPO_4$, 0.1% Triton X-100, 1.5% Polysorbate 80, 0.3% Lecithin in water, adjusted to pH 7.8 with 1 N HCl.

b) Exactly 60 minutes after inoculation, the Hilltop Chamber is removed from the site from which a sample is to be taken. A 8.6 cm$^2$ sampling cup in placed over thesite.

c) 5 ml of sampling solution is added to the cup.

d) Extract the bacteria by gently rubbing site with glass police man for 30 seconds.

e) Remove sampling solution with pipette and place in a sterile labeled test tube.

f) Repeat extraction with 5 ml of sampling fluid. This entire extraction procedure is repeated for each site 60 minutes after inoculation.

6. Quantifying Bacteria a) Prepare phosphate buffer solution of 0.117% $Na_2HPO_4$, 0.022% $NaH_2PO_4$, and 0.85% NaCl adjusted to pH 7.2–7.4 with 1 N HCl.

b) 1.1 ml of the sampling solution is aseptically removed from the tube, 0.1 ml of the solution is spread plated onto trypticase-soy agar containing 1.5% Polysorbate 80. Remaining 1 ml is placed into 9 ml of sterile phosphate buffer achieving a 1:10 dilution of the sampling solution. This process is repeated 3 more times (each serial dilution).

c) The plates are inverted and incubated for 24 hours at 35 C.

d) Colonies formed on plates are then enumerated and results are calculated by multiplying the counts by the dilution factor (original sample=10, first dilution=100, second dilution=1000, etc.) and the final results are reported as the number of colony forming units per ml (CFU's/ml).

7. Index Calculation

Gram Negative Residual Efficacy Index=$\log_{10}$(CFU's/ml of placebo site)–$\log_{10}$(CFU's/ml of test product site)

FOREARM CONTROLLED APPLICATION TEST (FCAT)

Reference: Ertel, K. D., et al.; "A Forearm Controlled Application Technique for Estimating the Relative Mildness of Personal Cleansing Products"; J. Soc. Cosmet. Chem. 46 (1995) 67–76

The Forearm Controlled Application Test, or FCAT, is a comparative test which discriminates differences in product mildness to the skin. A test product is compared to a standard soap based cleansing bar control.

Test Group Restrictions

Test groups of 20–30 subjects, 18 to 55 years of age, who regularly wash with soap are used. Potential subjects who (1) have an initial dryness grade of 3.0 or higher on the forearms as assessed during the initial examination, (2) have skin cancer, eczema, or psoriasis on the forearms, (3) are receiving injectable insulin, (4) are pregnant or lactating, or (5) are receiving treatment for skin problems or contact allergy are excluded. Subjects are to avoid hot tubs, swimming, and sun lamps, and to refrain from applying any soaps, cleansing products, creams, or gels to their forearms for the duration of the study. Subjects are to keep water off their forearms for at least two hours before the grading process. The studies are executed using a blinded, random product order format. Clinical assistant should verify the correct treatment sequence and document such before washing each subject.

Products are applied to the forearms a total of nine (9) times: two (2) times each day on the first four (4) days of the study and one (1) time on the final day. Visits to the test facility for washing must be spaced by a minimum of three (3) hours.

All clinical assistants must wear disposable gloves during wash procedure, rinsing them between treatments, and changing between subjects.

Control Product

| The control product is a rolled bar soap containing: | |
| --- | --- |
| 56.1% | Sodium Tallowate |
| 18.7% | Sodium Cocoate |
| 0.7% | Sodium Chloride |
| 24% | Water |
| 0.5% | Minors (Perfume, Impurities) |

Product Application Procedure

Both test and control products are tested on the same arm. The following test procedure is used.

1. The subject wets the entire surface of his/her volar forearm with 95–100° F. tap water by holding the arm briefly under running tap water.

2. A clinical assistant wets one-quarter sheet (approximately 8"×6") of Masslinn® towel with tap water, then squeezes the towel gently to remove excess water.

3. A clinical assistant applies the products to the arm, beginning with the product designated for the site nearest the elbow, using the appropriate procedure as follows:

Liquid Product a. Dispense 0.10 cc of test product from a syringe into the center of the appropriate marked area.

b. Wet two finders of gloved (latex) hand under the running tap (index and middle fingers).

c. Move wetted fingers in a circular motion over the application site for 10 seconds to lather product.

d. Lather remains on the application site for 90 seconds, then is rinsed off with running tap water for 15 seconds, taking care not to wash lather off the adjacent sites. After 10 seconds of the rinse has expired, the Clinical Assistant will gently rub the site being rinsed with her two gloved fingers for the remaining 5 seconds of the rinse.

Bar Product a. Wet two finders of gloved (latex) hand under the running tap (index and middle fingers).

b. Wet bar by holding bar briefly under running tap water. Test bars must be wet under a running tap at the start of each day.

c. Rub wetted fingers in a circular motion, over the surface of the bar, for 15 seconds to form lather on bar and fingers.

d. Rub the lathered fingers on the application site in a circular motion for 10 seconds to lather product on the skin.

e. Lather remains on the application site for 90 seconds, then is rinsed off with running tap water for 15 seconds, taking care not to wash lather off the adjacent sites. After 10 seconds of the rinse has expired, the Clinical Assistant will gently rub the site being rinsed with her two gloved fingers for the remaining 5 seconds of the rinse.

Wipe Products a. Fold wipe in half, crosswise, and gently rub the wipe in a curricular motion within the appropriate area.

b. Allow site to air dry for 90 seconds. Do not rinse site.
Leave-on Product
 a. Dispense 0.10 cc of test product from a syringe into the center of the appropriate marked area.
 b. Move gloved fingers in a circular motion over the application site for 10 seconds.
 c. Allow site to air dry for 90 seconds. Do not rinse site.
4. While waiting for the 90 second residence time to expire, the above procedure will be repeated on the remaining application site on that arm, working down the arm toward the wrist.
5. Steps 1–4 are repeated on the appropriate test areas so two applications of product are made to test areas.
6. After all of the application areas have two applications of products, the clinical assistant gently pats the subject's arm dry with a disposable paper towel.
Evaluation
 The skin on each treatment area is evaluated by an expert grader at baseline and three hours after the final study wash. The treatment areas are evaluated under 2.75× magnification (model KFM-1A Luxo Illuminated Magnifying Lamp, Marshall Industries, Dayton, Ohio) with controlled lighting (General Electric Cool White, 22-watt, 8" Circuline fluorescent bulb).
 The skin is evaluated by an expert grader, for dryness and a rating is assigned based on the definitions set forth below.

TABLE 1

Forearm Grading Scale

| Rating | Skin Dryness |
| --- | --- |
| 0 | No dryness |
| 1.0 | Patches of slight powderiness and occasional patches of small scales may be seen. |
| 2.0 | Generalized slight powderiness. Early cracking or occasional small lifting scales may be present. |
| 3.0 | Generalized moderate powderiness and/or heavy cracking and lifting scales. |
| 4.0 | Generalized heavy powderiness and/or heavy cracking and lifting scales. |
| 5.0 | Generalized high cracking and lifting scales. Eczematous change may be present. Powderiness may be present but not prominent. May see bleeding crack. |
| 6.0 | Generalized severe cracking. Eczematous change may be present. Bleeding cracks may be present. Scales large, may be beginning to disappear. |

The FCAT generally produces only mild to moderate skin irritation; however, if a treated site reaches a rating of 5.0 or greater, at any time during the study, treatment of all sites on that subject should be discontinued.
Data
 After all subjects have been evaluated at the end of the test, the following values are determined:

$Rc_o$=The average rating of control product area at baseline $Rc_f$=The average rating of control product area at test end $Rt_o$=The average rating of test product area at baseline $Rt_f$=The average rating if test product area at test end.

There are many external conditions which could influence the FCAT, such as relative humidity and water softness. The test is valid only if sufficient response is observed in the skin to the control product. The control response must be greater than 1.0 (i.e., $Rc_f-Rc_o \geq 1.0$) for the test to be valid.

Given a valid test, the Mildness Index of the test product is the difference in the skin responses to two products.

Mildness Index=$(Rc_f-Rc_o)-(Rt_f-Rt_o)$

CONSISTENCY (k) AND SHEAR INDEX (n) OF THE LIPOPHILIC SKIN MOISTURIZING AGENT

The Carrimed CSL 100 Controlled Stress Rheometer is used to determine Shear Index, n, and Consistency, k, of the lipophilic skin moisturizing agent used herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10–4 rad/sec, then this rate of strain is reported as a shear rate. These data are used to create a viscosity $\mu$ Vs. shear rate $\gamma'$ flow curve for the material. This flow curve can then be modeled in order to provide a mathematical expression that describes the material's behavior within specific limits of shear stress and shear rate. These results were fitted with the following well accepted power law model (see for instance: *Chemical Engineering* by Coulson and Richardson, Pergamon, 1982 or *Transport Phenomena* by Bird, Stewart and Lightfoot, Wiley, 1960):

$$\text{Viscosity}, \mu = k\ (\gamma')^{n-1}$$

VISCOSITY OF THE LIQUID PERSONAL CLEANSING COMPOSITION

The Wells-Brookfield Cone/Plate Model DV-II+ Viscometer is used to determine the viscosity of the liquid personal cleansing compositions herein. The determination is performed at 25° C. with the 2.4 cm° cone (Spindle CP-41) measuring system with a gap of 0.013 mm between the two small pins on the respective cone and plate. The measurement is performed by injecting 0.5 ml of the sample to be analyzed between the cone and plate and rotating the cone at a set speed of 1 rpm. The resistance to the rotation of the cone produces a torque that is proportional to the shear stress of the liquid sample. The amount of torque is read and computed by the viscometer into absolute centipoise units (mPa's) based on geometric constants of the cone, the rate of rotation, and the stress related torque.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

| Liquid Handsoap Component | EXAMPLE 1 Weight % | EXAMPLE 2 Weight % | EXAMPLE 3 Weight % |
| --- | --- | --- | --- |
| Ammonium Laureth-3 Sulfate | 9.5 | 5.5 | 6.6 |
| Ammonium Lauryl Sulfate | 3.2 | 2.9 | 3.1 |
| Sodium Lauroamphoacetate | 5.4 | 5.6 | 5.0 |

-continued

| Liquid Handsoap Component | EXAMPLE 1 Weight % | EXAMPLE 2 Weight % | EXAMPLE 3 Weight % |
|---|---|---|---|
| Citric Acid Anhydrous | 6.3 | 6.3 | 0.00 |
| polyacrylate* | 0.00 | 0.00 | 8.00 |
| Triclosan | 0.6 | 0.5 | 0.50 |
| Petrolatum | 16.5 | 12.0 | 12.0 |
| Tri-hydroxystearin | 0.15 | 0.15 | 0.25 |
| Lauric Acid | 1.0 | 1.5 | 1.5 |
| JR30M | 0.6 | 0.1 | 0.0 |
| Polyquaterium-10 | 0.0 | 0.0 | 0.1 |
| Sodium Hydroxide | 0.0 | 0.0 | to pH 4.0 |
| Sodium Citrate | to pH 3.9 | to pH 3.9 | 0.0 |
| Miscellaneous | 2.2 | 1.2 | 1.33 |
| Water | QS | QS | QS |
| K Value of Anionic Surfactant | <0.4 | <0.4 | <0.4 |
| Microtox of Anionic Surfactant | 1/150 | 1/150 | 1/150 |
| Biological Activity (Z) of acid | 1.29 | 1.29 | — |

*The polyacrylate is K7058 sold by B. F. Goodrich

The liquid handsoaps shown all have a Gram Negative Residual Effectiveness Index of greater than about 0.3 and a Mildness Index of greater than 0.3.

| Shower Gel Component | WEIGHT % 1 | WEIGHT % 2 | WEIGHT % 3 |
|---|---|---|---|
| Sodium or Ammonium Lauryl Sulfate | 6.30 | 3.15 | 3.15 |
| Sodium or Ammonium Laureth-3 Sulfate | 4.20 | 9.45 | 9.45 |
| Sodium or Ammonium Lauroamphoacetate | 5.25 | 5.40 | 5.40 |
| Cocoamide MEA | 2.80 | 0.00 | 0.00 |
| Citric Acid | 6.50 | 6.50 | 6.50 |
| Triclosan ® | 1.00 | 0.60 | 0.80 |
| Sodium Citrate | to pH 4 | to pH 3.5 | to pH 3.9 |
| Soybean Oil | 8.00 | 0.00 | 0.00 |
| Petrolatum | 0.00 | 16.50 | 16.5 |
| Dimethicone Emulsion | 0.00 | 0.00 | 1.00 |
| Trihydroxystearin | 0.00 | 1.0 | 1.0 |
| Lauric Acid | 0.00 | 1.0 | 1.0 |
| Palmitic Acid | 2.20 | 0.00 | 0.00 |
| Polyquaternium 10 | 0.30 | 0.60 | 0.30 |
| PEG 6 Caprylic/Capric Glycerides | 1.50 | 0.00 | 0.00 |
| Miscellaneous | 8.28 | 1.61 | 1.98 |
| Water | Q.S. | Q.S. | Q.S. |
| K Value of Anionic Surfactant | <0.4 | <0.40 | <0.40 |
| Microtox of Anionic Surfactant | 1/150 | 1/150 | 1/150 |
| Biological Activity (Z) of acid | 1.29 | 1.29 | 1.29 |

The shower gels shown all have a Gram Negative Residual Effectiveness Index of greater than about 0.3; and a Mildness Index of greater than 0.3.

Procedure for Making Handsoaps and Shower Gels

1. Handsoap Examples 1 and 2 and Shower Gel Examples 2 and 3

Add all ingredients except petrolatum, active and perfume together and heat to the point necessary to melt the stabilizer (approximately 190° F. for trihydroxystearin). Cool to below 115° F. and add active, petrolatum and perfume. Adjust final pH using NaOH or buffer salt. Add remaining water to complete product.

2. Shower Gel Example 1

Add moisturizing oils and co-surfactants together and heat ingredients to 130–140° F. until dissolved. In another container add primary surfactants, acid, buffer salt, preservatives, viscosity builder (salt), and polymer. Heat to 130–140° F. until dissolved. Combine two mixtures (or use single mixture if no oils are present) when both are 130–140° F., then begin cooling. When mixture is below 115° F., add, antibacterial active and perfume. Adjust final pH using NaOH or remaining buffer salt. Add remaining water to complete product.

What is claimed is:

1. A rinse-off antimicrobial cleansing composition comprising, by weight of the composition:
   a. from about 0.001% to about 5% of an antimicrobial active;
   b. from about 1% to about 80% of an anionic surfactant;
   c. from about 1% to about 12% of a proton donating agent;
   d. from about 0.1% to about 30% of a deposition aid; and
   e. from about 3% to about 98.8% of water;
   wherein the rinse-off antimicrobial cleansing composition is adjusted to a pH of from about 3.0 to about 6.0;
   wherein the rinse-off antimicrobial cleansing composition has a Gram Negative Residual Effectiveness Index of greater than about 0.3; and
   wherein the rinse-off antimicrobial cleansing composition has a Mildness Index of greater than 0.3.

2. A rinse-off antimicrobial cleansing composition according to claim 1 wherein the antimicrobial active is selected from the group consisting of triclosan, triclocarban, piroctone olamine, PCMX, ZPT, natural essential oils and their key chemical components, and mixtures thereof.

3. A rinse-off antimicrobial cleansing composition according to claim 2 wherein the antimicrobial active is triclosan.

4. A rinse-off antimicrobial cleansing composition according to claim 2 wherein the anionic surfactant has a solubility slope, K, of less than about 0.60 and has a Microtox Response Index of less than about 150.

5. A rinse-off antimicrobial cleansing composition according to claim 2 wherein the proton donating agent is an organic acid having a Biological Activity Index, Z, of greater than about 0.5.

6. A rinse-off antimicrobial cleansing composition according to claim 4 wherein the proton donating agent is an organic acid having a Biological Activity Index, Z, of greater than about 0.5.

7. A rinse-off antimicrobial cleansing composition according to claim 2 wherein the proton donating agent is a mineral acid.

8. A rinse-off antimicrobial cleansing composition according to claim 2 wherein the composition is adjusted to a pH of from about 3.5 to about 5.0.

9. A rinse-off antimicrobial cleansing composition according to claim 4 wherein the composition is adjusted to a pH of from about 3.5 to about 5.0.

10. A rinse-off antimicrobial cleansing composition according to claim 8 wherein the ratio of the amount of non-anionic surfactants to the amount of anionic surfactant is less than 1:1.

11. A rinse-off antimicrobial cleansing composition according to claim 9 wherein the ratio of the amount of non-anionic surfactants to the amount of anionic surfactant is less than 1:1.

12. A rinse-off antimicrobial cleansing composition comprising, by weight of the composition:
   a. from about 0.001% to about 5% of an antimicrobial active;
   b. from about 1% to about 80% of an anionic surfactant;
   c. from about 1% to about 12% of a proton donating agent;

d. from about 0.1% to about 30% of a lipophilic skin moisturizing agent;

e. from about 0.1% to about 10% of a stabilizer;

f. from about 3% to about 98.8% of water;

wherein the rinse-off antimicrobial cleansing composition is adjusted to a pH of from about 3.0 to about 6.0;

wherein the rinse-off antimicrobial cleansing composition has a Gram Negative Residual Effectiveness Index of greater than about 1.0; and wherein the rinse-off antimicrobial cleansing composition has a Mildness Index of greater than 0.4.

13. A rinse-off antimicrobial cleansing composition according to claim 12 comprising from about 5% to about 25% of the anionic surfactant.

14. A rinse-off antimicrobial cleansing composition according to claim 13 wherein the anionic surfactant has a solubility slope, K, of less than about 0.40 and has a Microtox Response Index of less than about 100.

15. A rinse-off antimicrobial cleansing composition according to claim 13 wherein the proton donating agent is an organic acid having a Biological Activity Index of greater than about 2.0.

16. A rinse-off antimicrobial cleansing composition according to claim 15 wherein the anionic surfactant is selected from the group consisting of sodium and ammonium alkyl sulfates and ether sulfates having chain lengths of predominantly 12 and 14 carbon atoms, olefin sulfates having chain lengths of predominantly 14 and 16 carbon atoms, and paraffin sulfonates having an average chain length of from 13 to 17 carbon atoms, and mixtures thereof.

17. A rinse-off antimicrobial cleansing composition according to claim 16 wherein the composition is adjusted to a pH of from about 3.5 to about 5.0.

18. A rinse-off antimicrobial cleansing composition according to claim 17 wherein the proton donating agent is selected from the group comprising adipic acid, tartaric acid, citric acid, maleic acid, malic acid, succinic acid, glycolic acid, glutaric acid, benzoic acid, malonic acid, salicylic acid, gluconic acid, polymeric acids, their salts, and mixtures thereof.

19. A rinse-off antimicrobial cleansing composition according to claim 18 wherein the ratio of the amount of non-anionic surfactants to the amount of anionic surfactant is less than 1:1.

20. A rinse-off antimicrobial cleansing composition according to claim 19 wherein the lipophilic skin moisturizing agent has a consistency (k) ranging from about 5 to about 5,000 poise and a shear index (n) ranging from about 0.01 to about 0.9.

21. A rinse-off antimicrobial cleansing composition according to claim 20 wherein the lipophilic skin moisturizing agent is selected from the group consisting of hydrocarbon oils and waxes, silicones, fatty acid esters, cholesterol, di-glycerides, triglycerides, liquid nondigestible oils, acetoglyceride esters, alkyl esters, alkenyl esters, lanolin, sterols, phospholipids, and mixtures thereof.

22. A rinse-off antimicrobial cleansing composition according to claim 21 wherein the lipophilic skin moisturizing agent comprises petrolatum.

23. A method for providing residual effectiveness against Gram negative bacteria comprising the use of a safe and effective amount of the composition of claim 1 on human skin.

24. A method for providing residual effectiveness against Gram negative bacteria which comprises the use of a safe and effective amount of the composition of claim 12 on human skin.

25. A method for treating acne comprising the use of a safe and effective amount of the composition of claim 1 on human skin.

26. A rinse-off antimicrobial cleansing composition according to claim 17 wherein the proton donating agent is selected from the group consisting of straight-chain poly (acrylic) acids and copolymers thereof, cross-linked poly (acrylic) acids having a molecular weight of less than about 250,000, poly ($\alpha$-hydroxy) acids and copolymers thereof, poly(methacrylic) acid and copolymers thereof, polysulfonic acid and copolymers thereof, carageenic acid, carboxy methyl cellulose, and alginic acid.

27. A rinse-off antimicrobial cleansing composition according to claim 1, wherein the ratio of the amount of non-anionic surfactants to the amount of anionic surfactant is less than about 1:2.

28. A rinse-off antimicrobial cleansing composition according to claim 13, wherein the ratio of the amount of non-anionic surfactants to the amount of anionic surfactant is less than about 1:2.

29. A rinse-off antimicrobial cleansing composition according to claim 13, wherein the stabilizer comprises a hydroxyl-containing fatty acid, fatty ester or fatty soap water-insoluble wax.

* * * * *